(12) United States Patent
Gronemann et al.

(10) Patent No.: US 11,512,033 B2
(45) Date of Patent: Nov. 29, 2022

(54) PROCESS AND PLANT FOR PRODUCING PURE METHANOL

(71) Applicant: L'Air Liquide, Société Anonyme pour l'Etude et l'Exploitation des Procédés Georges Claude, Paris (FR)

(72) Inventors: Veronika Gronemann, Karben (DE); Karin Huder, Frankfurt am Main (DE); Chin Han Lim, Frankfurt am Main (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 17/212,900

(22) Filed: Mar. 25, 2021

(65) Prior Publication Data
US 2021/0300852 A1  Sep. 30, 2021

(30) Foreign Application Priority Data
Mar. 26, 2020  (EP) .................................. 20020139

(51) Int. Cl.
*C07C 31/04* (2006.01)
*C07C 29/151* (2006.01)

(52) U.S. Cl.
CPC .......... *C07C 31/04* (2013.01); *C07C 29/1518* (2013.01)

(58) Field of Classification Search
CPC ........ C07C 29/151; C07C 29/76; C07C 31/04
See application file for complete search history.

(56) References Cited

U.S. PATENT DOCUMENTS

| 4,326,041 A | 4/1982 | Bahnisch |
| 5,827,901 A | 10/1998 | Konig et al. |
| 10,843,125 B2 * | 11/2020 | Raventos ................ C07C 31/04 |
| 10,874,983 B2 * | 12/2020 | Huder .................... B01D 53/74 |

(Continued)

FOREIGN PATENT DOCUMENTS

| DE | 29 34 332 | 3/1981 |
| DE | 32 20 995 | 12/1983 |
| EP | 0 790 226 | 8/1997 |

(Continued)

OTHER PUBLICATIONS

European Search Report for corresponding EP 20020139, dated Sep. 11, 2020.

(Continued)

*Primary Examiner* — Jafar F Parsa
(74) *Attorney, Agent, or Firm* — Elwood L. Haynes

(57) ABSTRACT

The invention relates to a process and a plant for producing pure methanol, wherein the crude methanol stream discharged from a methanol synthesis unit is decompressed in a decompression vessel, is subsequently at least partially freed of low-boiling by-products in a prerun column and is then supplied to a single- or multi-stage methanol purification apparatus from which a pure methanol product stream is finally discharged. According to the invention the tops product stream from the prerun column is subjected to a scrubbing step with a methanol-selective scrubbing medium, thus at least partially recovering methanol present and sending a methanol-depleted tops product stream to the offgas disposal apparatus.

7 Claims, 3 Drawing Sheets

(56) References Cited

U.S. PATENT DOCUMENTS

2018/0369745 A1 12/2018 Raventos et al.
2020/0282358 A1 9/2020 Huder et al.

FOREIGN PATENT DOCUMENTS

| EP | 1 016 643 | 7/2000 |
| EP | 3 181 540 | 6/2017 |
| EP | 3 181 541 | 6/2017 |
| WO | WO 2018 019875 | 2/2018 |

OTHER PUBLICATIONS

Methanol: The Basic Chemical and Energy Feedstock of the Future: Asinger's Vision Today, M. Bertau et al., eds., Springer-Verlag, Berlin, 2014 e-Book, 264-265.
Ullmann's Encyclopedia of Industrial Chemistry, $6^{th}$ ed. 1998 electronic release, Ch. 5.2, Synthesis, 620-621.

\* cited by examiner

PROCESS AND PLANT FOR PRODUCING PURE METHANOL

CROSS REFERENCE TO RELATED APPLICATIONS

This application claims the benefit of priority under 35 USC 119 (a) and (b) to EP 20020139.0, filed Mar. 26, 2020, the entire contents of which are incorporated herein by reference.

BACKGROUND

Field of the Invention

The invention relates to a process and a plant for producing pure methanol, wherein the crude methanol stream discharged from a methanol synthesis unit is decompressed in a decompression vessel, is subsequently at least partially freed of low-boiling by-products in a prerun column and is then supplied to a single- or multi-stage methanol purification apparatus from which a pure methanol product stream is finally discharged.

Prior Art

Methanol (MeOH) is an important organic commodity chemical and is used in the chemical industry inter glia as a starting material for producing formaldehyde, formic acid and acetic acid and also as a starting product for producing olefins. Industrial methanol production is typically carried out under heterogeneous catalysis from carbon oxides and hydrogen.

Processes for production of methanol by catalytic reaction of synthesis gas containing hydrogen and carbon oxides have long been known to those skilled in the art.

In one known embodiment, the methanol is produced in a circular process wherein a mixture of fresh and partially reacted synthesis gas is supplied initially to a water-cooled reactor and then to a gas-cooled reactor, in each of which the synthesis gas is converted into methanol over a copper catalyst. The methanol produced in the process is separated from the synthesis gas to be recycled which is then passed through the gas-cooled reactor in countercurrent as coolant and preheated to a temperature of 220° C. to 280° C. before it is introduced into the first synthesis reactor. A portion of the synthesis gas to be recycled, which is small relative to the gas inventory present in the system, is removed from the process as a purge stream in order to prevent inert components, impurities or by-products from being enriched within the synthesis gas circuit. This measure is also taught in German laid-open specification DE 2934332 A1 and European patent application EP 1016643 A1.

Crude methanol from methanol synthesis still contains water, higher alcohols, further impurities and other light constituents. In order to produce methanol according to market specifications the crude methanol must be purified by distillation.

As described in another embodiment known in the art, the distillative workup of crude methanol comprises initially expelling dissolved gases, for example carbon oxides, hydrogen and methane, by decompressing the crude methanol by introduction into an expansion vessel. The removal of the low boilers, for example ethers, formates, aldehydes, ketones and the remaining dissolved gases is carried out in a prerun column. The methanol is subsequently separated from the heavy constituents such as ethanol, higher alcohols and water in a pure methanol distillation plant consisting of one or two columns. The two-column process comprising a prerun column and a pure methanol column has advantages in terms of capital expenditure savings while the three-column process which comprises a high-pressure column and an atmospheric-pressure column for obtaining pure methanol in addition to the prerun column has advantages in terms of energy consumption and is suitable for large production capacities in particular.

The offgas from the prerun column still contains some methanol that cannot be condensed since otherwise the low boilers removed using the prerun column would likewise condense and become enriched therein. The processes for distillative purification of crude methanol hitherto known from the prior art therefore have the disadvantage that methanol losses are incurred when the offgas is thermally recovered via a flare system or that methanol passes into the atmosphere if no flare system is available.

One or more reservoir vessels in which the methanol may be intermediately stored in case of maintenance are also provided in the distillation plants. These reservoir vessels must be purged with an inert gas, often with nitrogen, to ensure that no methanol accumulates in the vapour phase. Here too, the methanol-laden inert gas/purge gas is discharged as an offgas and disposed of which in turn leads to methanol losses.

SUMMARY

The present invention thus has for its object to specify a process and a plant for production of pure methanol which does not exhibit the recited disadvantages of the prior art.

This object is solved in a first aspect by a process having the features of claim 1. Further embodiments of the invention are apparent from the subsidiary claims of the respective category.

Methanol synthesis conditions are known to those skilled in the art from the prior art, for example the documents discussed at the outset. These are the physicochemical conditions under which a measurable, preferably industrially relevant, conversion of synthesis gas constituents to methanol is achieved. Necessary adjustments of these conditions to the respective operational requirements will be made on the basis of routine experiments. Any specific reaction conditions disclosed may serve here as a guide, but they should not be regarded as limiting in relation to the scope of the invention.

In the context of the present invention a division or resolution/separation of a material stream is to be understood as meaning production of at least two substreams from the original material stream, wherein resolution/separation is associated with an intentional alteration of the composition of matter of the obtained substreams with respect to the original material stream, for example through application of a thermal separation process to the original material stream. By contrast, division of the original material stream is generally not associated with a change in the composition of matter of the obtained substreams.

Enrichment or depletion of a component in a mixture, a fraction or a material stream is to be understood as meaning a measure, operation or process step which has the result that the mole fraction or mass fraction of this component increases (enrichment) or decreases (depletion).

The predominant portion of a fraction, of a material stream, etc. is to be understood as meaning a proportion quantitatively greater than all other proportions each considered alone. Especially in the case of binary mixtures or in the case of resolving a fraction into two parts this is to be understood as meaning a proportion of more than 50% by weight unless otherwise stated in the specific case.

The indication that a material stream consists predominantly of one component or group of components is to be understood as meaning that the mole fraction or mass fraction of this component or component group is quantitatively greater than all other proportions of other components or component groups in the material stream each considered alone. Especially in the case of binary mixtures this is to be understood as meaning a proportion of more than 50%. Unless otherwise stated in the specific case this is based on the mass fraction.

All approximate pressures are reported in absolute pressure units, bar for short, or in gauge pressure units, barg for short, unless otherwise stated in the particular individual context.

Fluid connection between two regions of the apparatus according to the invention is to be understood as meaning any type of connection whatsoever which makes it possible for a fluid, for example a gas stream, to flow from one to the other of the two regions, neglecting any interposed regions or components. In particular a direct fluid connection is to be understood as meaning any type of connection whatsoever which makes it possible for a fluid, for example a gas stream, to flow directly from one to the other of the two regions, wherein no further regions or components are interposed. One example would be a pipeline leading directly from one to the other of the two regions.

A means is to be understood as meaning something that enables or is helpful in the achievement of a goal. In particular, means for performing a particular process step are to be understood as including all physical articles that would be considered by a person skilled in the art in order to be able to perform this process step. For example, a person skilled in the art will consider means of introducing or discharging a material stream to include all transporting and conveying apparatuses, i.e. for example pipelines, pumps, compressors, valves, which seem necessary or sensible to said skilled person for performance of this process step on the basis of his knowledge of the art.

The indication that two or more compressor stages are connected or arranged parallel is to be understood as meaning that a material stream which passes through one of the compressor stages and is compressed therein does not additionally pass through one of the other compressor stages to be compressed therein, wherein the two or more compressor stages may be operated independently of one another.

An offgas disposal apparatus is to be understood as meaning an apparatus operating according to a principal of offgas aftertreatment or offgas purification. The offgas disposal apparatus also comprises means for discharging the offgases from their site of generation and sending them for offgas aftertreatment or offgas purification, for example pipelines. Combustion, for example in a flare system, is often a suitable disposal method for flammable offgases. For less concerning offgas types discharging to the environment, for example via a chimney, may also be a suitable disposal method if this complies with statutory emissions limits.

A methanol purification apparatus is to be understood as meaning an apparatus by means of which methanol may be worked up to afford a pure methanol product in a multistage distillation process. These include in particular the two-column processes discussed at the outset and comprising a prerun column and a pure methanol column and the three-column processes comprising a high-pressure column and an atmospheric-pressure column for obtaining pure methanol in addition to the prerun column.

The present invention provides for maximizing the methanol yield. This is effected, in addition to other measures, in a first aspect of the invention by providing an offgas scrubbing which does not remove and thus does not enrich the low boilers but rather selectively recovers the methanol which in one embodiment of the invention is recycled from the bottom of the scrubbing apparatus to the inlet of the prerun column.

A second aspect of the process according to the invention is characterized in that water is used as the scrubbing medium. Water as a scrubbing medium is usually cheap, environmentally neutral and available in different purities. Methanol-laden aqueous scrubbing medium may easily be recycled into the workup of the crude methanol since with methanol and water it comprises components intrinsic to the process.

A third aspect of the process according to the invention is characterized in that methanol-laden water is discharged from the scrubbing apparatus and recycled to the prerun column. For example in the case of the three-column process comprising a prerun column, high-pressure column and atmospheric-pressure column traversed in this sequence it is most advantageous to recycle the laden water to the prerun column since said column separates the low boilers first. Water and high boilers are then separated in the high-pressure and atmospheric-pressure columns.

A fourth aspect of the process according to the invention is characterized in that methanol-laden water is discharged from the scrubbing apparatus and introduced to the methanol purification apparatus. This makes it possible for existing apparatuses for workup of the crude methanol to afford pure methanol to also be utilized for recovery of the methanol from the methanol-laden water. A significant enlargement of the methanol purification apparatus is generally not required since the amount of substance stream of the methanol-laden water is usually small compared to the stabilized methanol stream entering the methanol purification apparatus as the bottoms product stream from the prerun column.

A fifth aspect of the process according to the invention is characterized in that the gaseous tops product stream comprising synthesis gas constituents from the decompression vessel is subjected to a scrubbing step with a methanol-selective scrubbing medium in a scrubbing apparatus. The tops product stream from the decompression vessel also still contains methanol proportions which are expediently recoverable in this way. The combination of the methanol recovery from the tops product of the prerun column with that from the tops product stream from the decompression vessel increases the proportion of altogether recovered methanol.

A sixth aspect of the process according to the invention is characterized in that the methanol purification apparatus comprises at least one methanol reservoir vessel whose free gas space is purged with an inert gas, wherein the methanol-laden inert gas is discharged from the at least one methanol reservoir vessel and subjected to a scrubbing step with a methanol-selective scrubbing medium in a scrubbing apparatus. Such a methanol separation from the inert gas purge gas of methanol reservoir vessels is described for example in the European patent specifications EP 3181540 B1 and EP 3181541 B1. The combination of the methanol recovery from the tops product of the prerun column with that from the inert gas purge gas of the methanol reservoir vessel(s) increases the proportion of altogether recovered methanol. In a development of this concept the methanol recovery may be maximized by combining the methanol recovery from the tops product of the prerun column with that from the inert gas purge gas of the methanol reservoir vessel(s) and that from the tops product stream from the decompression vessel.

A seventh aspect of the process according to the invention is characterized in that at least two of the scrubbing steps are performed with the same scrubbing medium in a common scrubbing apparatus. This makes it possible to increase or maximize the methanol recovery while being able to save on apparatuses and equipment parts on account of the common utilization.

In a further aspect the plant according to the invention further comprises means for discharging methanol-laden scrubbing medium from the at least one scrubbing apparatus and means for recycling same into the prerun column. The advantages of this aspect of the plant according to the invention correspond to those described in connection with the third aspect of the process according to the invention.

In a further aspect the plant according to the invention further comprises means for discharging methanol-laden scrubbing medium from the at least one scrubbing apparatus and means for supplying same to the methanol purification apparatus. The advantages of this aspect of the plant according to the invention correspond to those described in connection with the fourth aspect of the process according to the invention.

In a further aspect the plant according to the invention further comprises means for supplying the gaseous tops product stream comprising synthesis gas constituents from the decompression vessel to the at least one scrubbing apparatus and means for discharging a methanol-depleted gas stream from the at least one scrubbing apparatus. The advantages of this aspect of the plant according to the invention correspond to those described in connection with the fifth aspect of the process according to the invention.

In a further aspect the plant according to the invention is characterized in that the methanol purification apparatus comprises at least one methanol reservoir vessel whose free gas space is purgable with an inert gas, wherein the plant further comprises means for discharging the methanol-laden inert gas from the methanol reservoir vessel and for supplying same to the at least one scrubbing apparatus. The advantages of this aspect of the plant according to the invention correspond to those described in connection with the sixth aspect of the process according to the invention.

In a further aspect the plant according to the invention is characterized in that the at least one scrubbing apparatus is configured such that at least two methanol-laden gas streams selected from the following group may be scrubbed therein simultaneously: tops product stream from the prerun column, tops product stream from the decompression vessel, inert gas from the methanol reservoir vessel. The advantages of this aspect of the plant according to the invention correspond to those described in connection with the seventh aspect of the process according to the invention.

BRIEF DESCRIPTION OF THE DRAWINGS

Developments, advantages and possible applications of the invention are also apparent from the following description of working and numerical examples and the drawings. All features described and/or depicted form, either in themselves or in any combination, the invention, regardless of the way they are combined in the claims or the back-references therein.

DETAILED DESCRIPTION OF PREFERRED EMBODIMENTS

Figure 1:
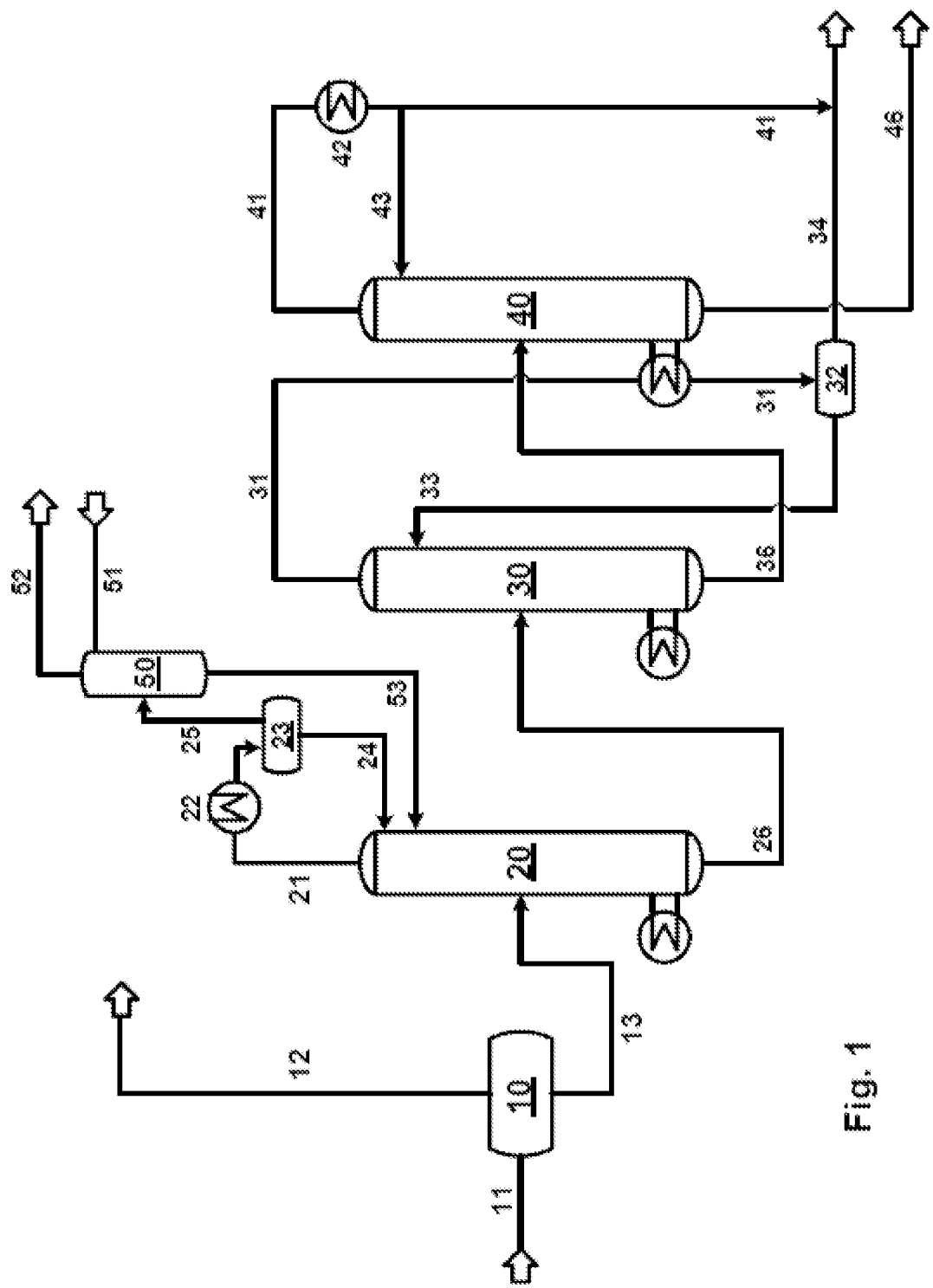
FIG. 1 is a first example of a process/a plant for production of pure methanol according to the invention.

In the inventive working example shown in FIG. 1 crude methanol obtained by at least partial conversion of a synthesis gas containing hydrogen and carbon oxides under methanol synthesis conditions in an undepicted methanol synthesis unit containing at least one methanol synthesis reactor is passed via conduit 11 into a decompression vessel 10 and therein decompressed from an initial pressure of typically 75 bara to a final pressure of typically 6 bara. Gases dissolved in the crude methanol are liberated and via conduit 12 as the tops product stream from the decompression vessel sent to an undepicted offgas disposal.

Via conduit 13 a liquid, decompressed crude methanol stream depleted in synthesis gas constituents is discharged from the decompression vessel as the bottoms product stream and introduced to a prerun column 20. This performs a distillative resolution of the crude methanol stream depleted in synthesis gas constituents under conditions known to those skilled in the art. A gaseous, tops product stream comprising low-boiling by-products and methanol vapour is discharged from the prerun column via conduit 21. After cooling of same in a cooler 22 and partial condensation a phase separation is carried out in a gas-liquid phase separator 23. A liquid condensate stream is recycled therefrom to the prerun column via conduit 24 and a gas stream is discharged therefrom via conduit 25. According to the invention this gas stream is introduced via conduit 25 to a scrubbing apparatus 50 and therein scrubbed with water as a methanol-selective scrubbing medium which is supplied via conduit 51 and introduced to the scrubbing apparatus in the upper region thereof, preferably at the top end thereof. The industrial performing of this scrubbing process is known per se to those skilled in the art. Details are moreover derivable from the relevant literature, for example the two abovementioned EP patent specifications EP 3181540 B1 and EP 3181541 B1.

In the working example of FIG. 1 the methanol-laden scrubbing medium is recycled to the prerun column via conduit 53 and introduced thereto. Via conduit 52 the gas stream freed of methanol and containing low-boiling by-products from the methanol synthesis is discharged from the scrubbing apparatus and sent to the offgas disposal. This preferably comprises a flare system so that flammable, low-boiling by-products of the methanol synthesis may also be thermally recovered and thus discharged to the environment in environmentally neutral fashion.

Via conduit 26 a liquid, stabilized methanol stream depleted in low-boiling by-products is discharged from the prerun column as the bottoms product stream and introduced to a high-pressure column 30 which is operated at a pressure of typically 8.6 bara. This performs distillative separation of pure methanol as a vaporous tops product which is discharged via conduit 31. Arranged in the conduit path 31 is a heat exchanger which is used for heating a downstream atmospheric column 40, wherein the pure methanol vapour discharged from the high-pressure column is used as the heating medium and thus simultaneously cooled and partially condensed. The resulting phase separation and the management of the vapour phase are undepicted for the sake of simplicity. Via conduit 31, container 32 and conduit 34 a liquid pure methanol stream is discharged from the process/ the plant as the target product. Via conduit 33 a pure methanol substream is recycled to the high-pressure column.

The methanol- and water-containing bottoms product stream from the high-pressure column is discharged therefrom via conduit 36 and introduced into the atmospheric column 40. This performs the further distillative resolution of the methanol-water mixture at atmospheric pressure and under other conditions known to those skilled in the art. The resulting predominantly water-containing bottoms product is discharged from the column 40 via conduit 46 and sent to an undepicted wastewater disposal.

Via conduit 41 a pure methanol vapour stream is discharged from the column 40 and subsequently cooled and thus partially condensed in cooler 42. The resulting phase separation and the management of the vapour phase are undepicted for the sake of simplicity. A substream of the pure methanol condensate is recycled via conduit 43 to the column 40 as a reflux stream and applied in the upper region thereof. The remaining pure methanol condensate is added to the liquid pure methanol stream via conduits 41 and 34.

Figure 2:
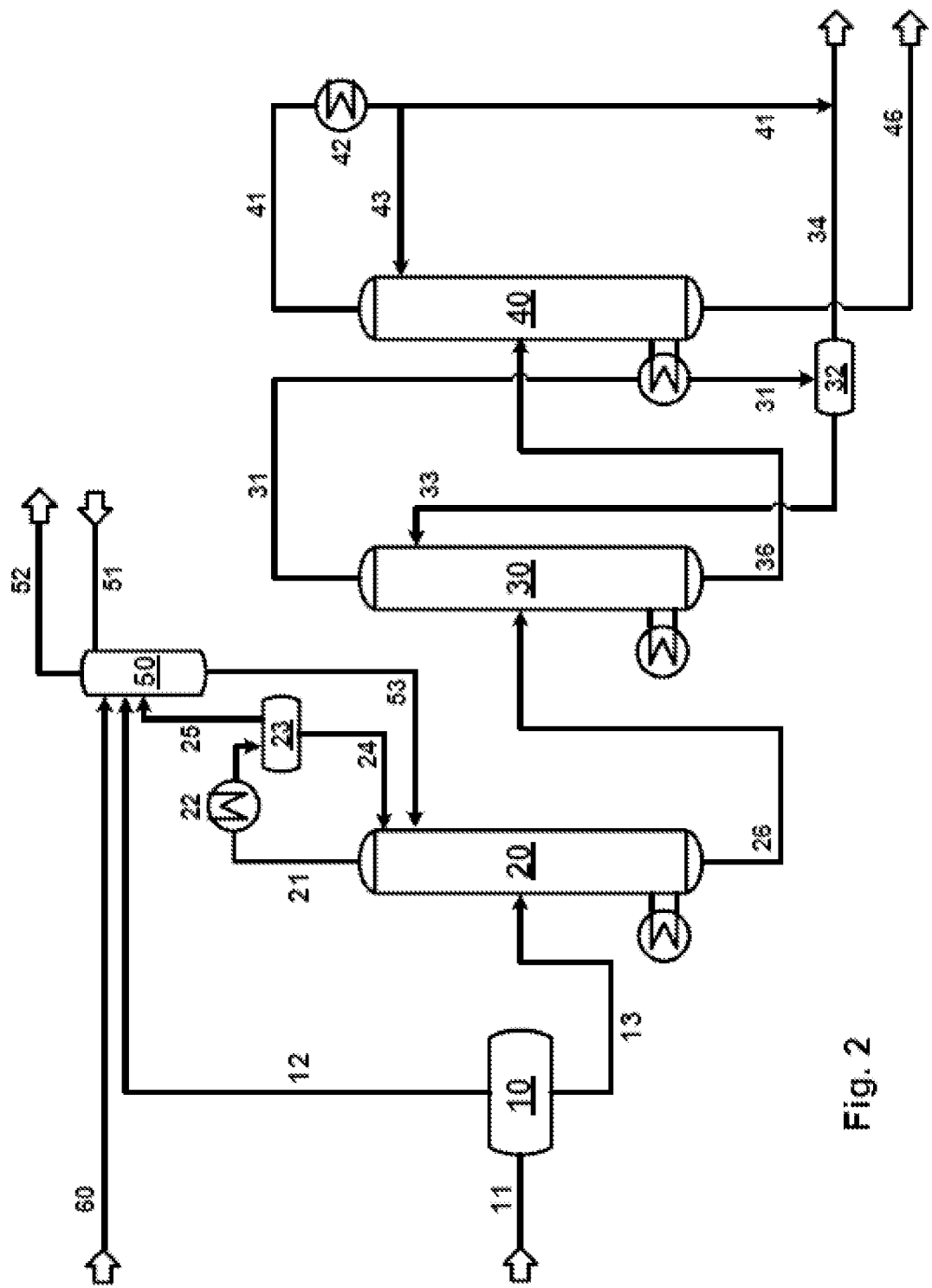
FIG. 2 is a second example of a process/a plant for production of pure methanol according to the invention.

In addition to the working example of FIG. 1, in the working example of the invention shown in FIG. 2 the tops product stream from the decompression vessel containing the gases dissolved in the crude methanol is also discharged via conduit 12 and passed to the scrubbing apparatus 50 and introduced thereto. Furthermore, a methanol vapour-laden purge gas stream which was previously discharged from an undepicted methanol reservoir vessel is passed to the scrubbing apparatus 50 and introduced thereto via conduit 60. This has the advantage that the scrubbing apparatus may also be used to remove methanol from the gas streams passed through conduits 12 and 60 without any need to provide additional separate scrubbing apparatuses. It is also possible for either only the gas stream in conduit 12 or only the gas stream in conduit 60 to be passed to the scrubbing apparatus 50.

Figure 3:
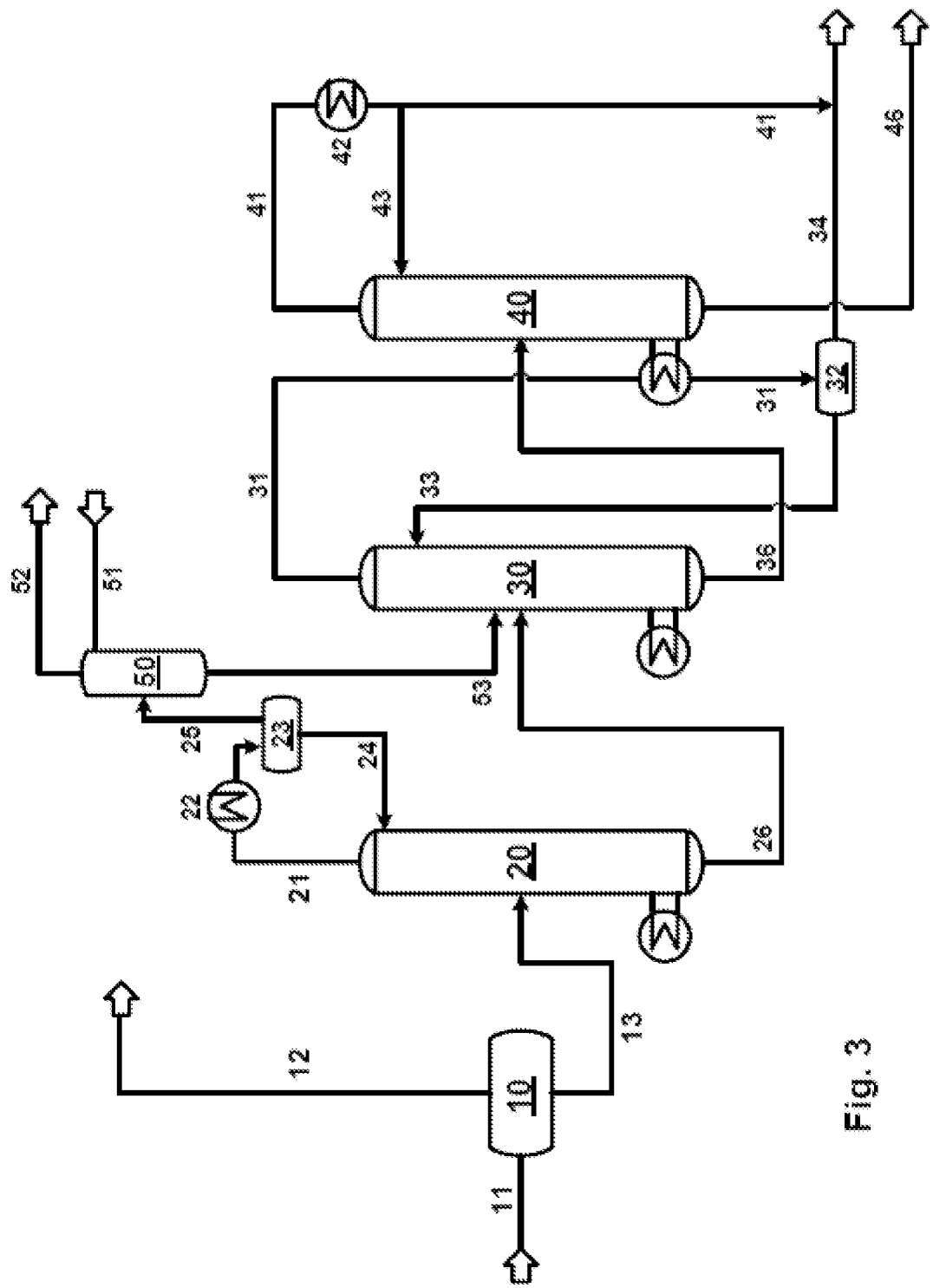
FIG. 3 is a third example of a process/a plant for production of pure methanol according to the invention.

In a departure from the working example of FIG. 1, in the working example of the invention shown in FIG. 3 the bottoms product stream containing the methanol-laden scrubbing medium which is discharged from the scrubbing apparatus 50 via conduit 53 is passed to the high-pressure column 30 and introduced thereto. This working example may also be modified such that, similarly to the working example of FIG. 2, the gas stream in conduit 12 and/or a methanol vapour-laden purge gas stream from a methanol reservoir vessel (FIG. 2, conduit 60) are also passed to the scrubbing apparatus 50. A further option comprises applying a substream of the methanol-laden scrubbing medium from the scrubbing apparatus 50 to each of the prerun column and the high-pressure column. This allows the overall process to be more sensitively controlled, for example in the case of bringing online or process alterations.

Example

The process according to the invention was performed according to the embodiment shown in FIG. 1. The gas stream discharged from the prerun column via conduit 25 was introduced into the scrubbing apparatus 50, which was configured as a scrubbing column comprising random packings or trays, and scrubbed with demineralized water therein. Around 90% by weight of the methanol was recovered as liquid while all dissolved gases still passing into the prerun column and more than 80% by weight of the low boners exited the scrubbing apparatus overhead and were sent to the offgas disposal.

LIST OF REFERENCE SIGNS

10 Decompression vessel
11 Conduit
12 Conduit
13 Conduit
20 Prerun column
21 Conduit
22 Cooler
23 Gas-liquid phase separator
24 Conduit
25 Conduit
26 Conduit
30 High-pressure column
31 Conduit
32 Container
33 Conduit
34 Conduit
36 Conduit
40 Atmospheric-pressure column
41 Conduit
42 Cooler
43 Conduit
46 Conduit
50 Scrubbing apparatus
51 Conduit
52 Conduit
53 Conduit
60 Conduit It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing pure methanol from a synthesis gas containing hydrogen and carbon oxides as synthesis gas constituents, comprising:
   (a) at least partially converting the synthesis gas containing hydrogen and carbon oxides under methanol synthesis conditions in a methanol synthesis unit containing at least one methanol synthesis reactor,
   (b) discharging a liquid crude methanol stream containing methanol, water, dissolved synthesis gas constituents and low-boiling by-products from the methanol synthesis unit,
   (c) introducing the liquid crude methanol stream into a decompression vessel, discharging a liquid, decompressed crude methanol stream depleted in synthesis gas constituents as the bottoms product and a gaseous tops product stream comprising synthesis gas constituents from the decompression vessel,
   (d) introducing the liquid, decompressed crude methanol stream depleted in synthesis gas constituents to a prerun column, distillatively resolving said stream, discharging a liquid, stabilized, methanol stream depleted in low-boiling by-products as the bottoms product stream and a gaseous tops product stream comprising low-boiling by-products and methanol vapour from the prerun column, (e) introducing the bottoms product stream from the prerun column to a single- or multi-stage methanol purification apparatus, discharging a pure methanol product stream from the methanol purification apparatus, (f) sending the tops product stream from the prerun column to an offgas disposal apparatus, wherein, (g) before sending to the offgas disposal apparatus, the tops product stream from the prerun column is subjected to a scrubbing step with a methanol-selective scrubbing medium in a scrubbing apparatus and a methanol-depleted tops product stream is sent to the offgas disposal apparatus.

2. The process according to claim 1, wherein water is used as the scrubbing medium.

3. The process according to claim 2, wherein methanol-laden water is discharged from the scrubbing apparatus and recycled to the prerun column.

4. The process according to claim 2, wherein methanol-laden water is discharged from the scrubbing apparatus and introduced to the methanol purification apparatus.

5. The process according to claim 1, wherein the gaseous tops product stream comprising synthesis gas constituents from the decompression vessel is subjected to a scrubbing step with a methanol-selective scrubbing medium in a scrubbing apparatus.

6. The process according to claim 1, wherein the methanol purification apparatus comprises at least one methanol reservoir vessel whose free gas space is purged with an inert gas, wherein the methanol-laden inert gas is discharged from the at least one methanol reservoir vessel and subjected to a scrubbing step with a methanol-selective scrubbing medium in a scrubbing apparatus.

7. The process according to claim 1, wherein at least two of the scrubbing steps are performed with the same scrubbing medium in a common scrubbing apparatus.

* * * * *